United States Patent
AlDahian et al.

(10) Patent No.: US 9,204,955 B2
(45) Date of Patent: Dec. 8, 2015

(54) SURGICAL MESH WITH INTEGRATED THREADS

(71) Applicant: King Saud University, Riyadh (SA)

(72) Inventors: Abdullah Dahian AlDahian, Riyadh (SA); Feras Mohammad AlShomer, Riyadh (SA)

(73) Assignee: King Saud University, Riyadh (SA)

( * ) Notice: Subject to any disclaimer, the term of this patent is extended or adjusted under 35 U.S.C. 154(b) by 190 days.

(21) Appl. No.: 13/853,159

(22) Filed: Mar. 29, 2013

(65) Prior Publication Data
US 2014/0296885 A1   Oct. 2, 2014

(51) Int. Cl.
*A61B 17/08*   (2006.01)
*A61F 2/00*    (2006.01)

(52) U.S. Cl.
CPC ....... *A61F 2/0063* (2013.01); *A61F 2002/0068* (2013.01)

(58) Field of Classification Search
None
See application file for complete search history.

(56) References Cited

U.S. PATENT DOCUMENTS

| | | | |
|---|---|---|---|
| 3,054,406 A | 9/1962 | Usher | |
| 5,456,720 A | 10/1995 | Schultz et al. | |
| 6,551,356 B2 | 4/2003 | Rousseau | |
| 6,755,867 B2 | 6/2004 | Rousseau | |
| 7,766,926 B2 * | 8/2010 | Bosley et al. | 606/151 |
| 2011/0130774 A1 | 6/2011 | Criscuolo et al. | |
| 2011/0184441 A1 * | 7/2011 | St-Germain | 606/151 |
| 2011/0295283 A1 * | 12/2011 | Darois et al. | 606/151 |

FOREIGN PATENT DOCUMENTS

JP    2011115588 A    6/2011

\* cited by examiner

*Primary Examiner* — Gregory Anderson
*Assistant Examiner* — Robert Lynch
(74) *Attorney, Agent, or Firm* — Hauptman Ham, LLP

(57) ABSTRACT

A surgical mesh of the type used in laparoscopic surgery and repair of inguinal hernias includes a compact roll of planar overlay material of woven fibers. The planar overlay material includes a plurality of outwardly extending integral threads for grasping with a surgical instrument and spreading over a tissue deficiency. In addition, a plurality of integral threads are provided for transfixation of said overlay material to surrounding tissue. Further, the woven fibers are selected from the group consisting of nylon, polyester, polypropylene fibers and mixtures thereof and in which the outwardly extending threads for grasping have a length of about ½ to 1 cm and the transfixation threads have a length of about 3 cm to 4 cm. In addition, the grasping threads extend outwardly from both sides of the mesh while the transfixation threads extend outwardly from only one side thereof.

3 Claims, 2 Drawing Sheets

SURGICAL MESH WITH INTEGRATED THREADS

FIELD OF THE INVENTION

This invention relates to surgical mesh with integrated threads and more particularly to surgical mesh for the correction of inguinal hernias and other surgical interventions.

BACKGROUND FOR THE INVENTION

Surgical mesh has been used for many years in a vast number of surgical interventions. It is basically a thin delicate sheet with a smooth surface that is manufactured from different materials with various orientations of the intersections for more elasticity. The surgical mesh is applied in a wide variety of wounds or tissues to aid in supporting and reinforcing the soft tissue that has been weakened in a human being.

The Food and Drug Administration (FDA) has reported that more than one million hernia repairs are performed each year in the United States and of these approximately 800,000 are for inguinal hernias that occur in the inner groin. Approximately 90% of such repairs involve mesh based repairs that typically result in reduced recurrence rates, decreased operative time and minimized recovery time.

In laparoscopic surgery small incisions are used to insert instruments that are manipulated from the outside of a human body under the visualization of a camera to grasp, cut or dissect tissue. The surgical mesh is inserted through a small incision and manipulated inside the body using different instruments. The manipulation involves a lot of fine movement to open and spread the mesh.

A ventral hernia repair is disclosed in a U.S. Patent Publication Application No. 2011/0130774 of Criscuolo et al. wherein a compact roll of mesh is inserted into a human body. As disclosed, a compact roll of mesh has a distal end attached to a needle with the needle oriented substantially parallel to the longitudinal axis of the rolled mesh. A laparoscopic device is configured and dimensioned to transfer the rolled mesh into a body cavity and means for unrolling and laying the rolled surgical mesh under a ventral hernia in an abdominal wall is also provided. The reference also discloses means for threading the needle and for making a suture through the surgical mesh and the abdominal wall as well as means for trimming the suture.

A U.S. Pat. No. 6,551,356 of Rousseau, discloses a device for surgically repairing and reinforcing a hernia. The device includes a hernia prosthesis having a substantially planar base portion and an overlay portion, each formed from a biocompatible material. The overlay portion is peripherally attached to the base portion to define a pocket to receive a surgical instrument or a surgeon's finger for placing the prosthesis within the human body. The pocket may be formed with releasable stitching to enable it to be flattened or removed after placement and maintain a resilient member that urges the prosthesis into a flat configuration.

A second U.S. Pat. No. 6,755,867 of Rousseau, discloses a hernia repair prosthesis with an occlusive member for inserting and/or backing the herniated tissue. An overlay sheet is attached to the occlusive member by a filament which permits the occlusive member and the overlay sheet to slide relative to one another along the filament allowing the maximal positioning of the overlay sheet to provide the best surgical attachment, orientation and alignment with a patient's anatomy.

Notwithstanding the above, it is presently believed that there is a need and potential commercial market for an improved surgical mesh with integrated threads in accordance with the present invention. There should be a need and a commercial market for mesh in accordance with the present invention because such mesh provides faster surgical procedures with less trauma to a patient, reduced rates of infection and speedier recoveries.

BRIEF SUMMARY OF THE INVENTION

In essence the present invention comprises or consists of surgical mesh with integrated gripping and fixating threads and more particularly to a compact roll of surgical mesh i.e. a planar overlay material that includes or consists of woven fibers with a plurality of outwardly extending integral threads for grasping with a surgical instrument, spreading over a tissue deficiency and for transfixing (tying) the planar overlay material to surrounding tissues.

In a preferred embodiment of the invention the woven fibers are selected from the group consisting of nylon, polyester, polypropylene fibers and mixtures thereof. Further, the outwardly extending threads are selected from the same material while the threads for grasping have lengths of about ½ cm and about 1 cm and the transfixation threads have a length of about 3 cm and about 4 cm.

A further embodiment of the invention contemplates a method for repairing a tissue deficiency in a human body such as an inguinal hernia. The method comprises or consists of providing a compact roll of surgical mesh with integrated gripping and/or fixation threads and more particularly to a compact roll of surgical mesh i.e. a planar overlay material of woven fibers in which the planar overlay material comprises or consists of a plurality of outwardly extending integral threads for grasping with a surgical instrument and spreading over a tissue deficiency and for transfixing (tying) the planar overlay material to surrounding tissue selected from the group consisting of nylon, polyester, polypropylene fibers and mixtures thereof. The grasping threads have a length of between about ½ to about 1 cm and the transfixation threads have a length of about 3 cm to 4 cm.

The aforementioned compact roll is inserted through a tube into a human body. The integral grasping threads are grasped with a surgical instrument and spread and positioned over a tissue deficiency. In the next step, the planar overlay material is transfixed using the integral transfixing threads to surround tissue adjacent to a tissue deficiency. Finally, the instruments are removed from the patient and the small incision closed.

The invention will now be described in connection with the accompanying figures.

Figure 1:
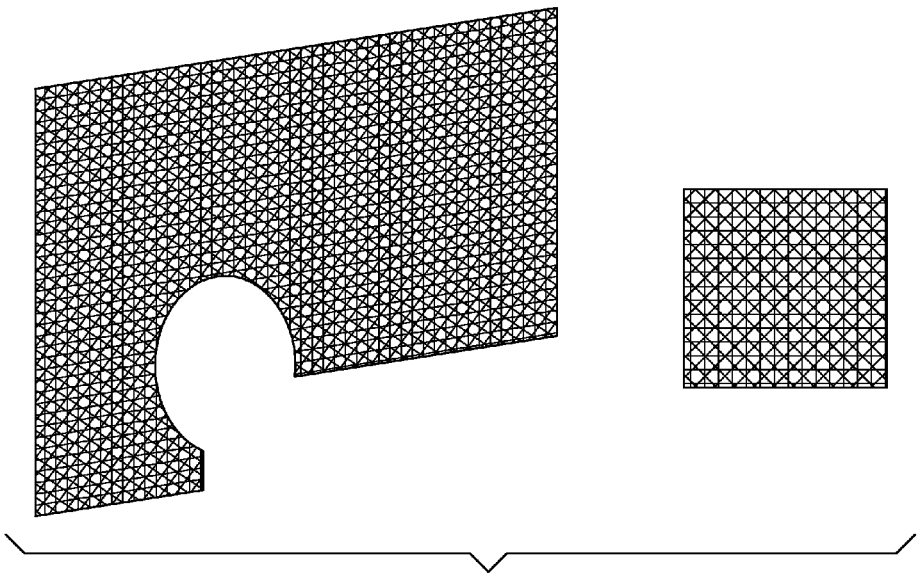
FIG. 1 is a schematic illustration of a piece of mesh in accordance with one embodiment of the invention.

DESCRIPTION OF THE PREFERRED
EMBODIMENTS OF THE INVENTION

Surgical mesh has for many years been used in many surgical interventions. Such mesh has been manufactured from different compositions as well as in different sizes and shapes to be used in different parts of the human body. One of the more common uses is the repair of inguinal hernias that occur in the inner groin.

The surgical mesh in accordance with the present invention is believed to be particularly applicable to the repair of inguinal hernias which will be emphasized in the following discussions.

After the mesh is positioned over an area of defect, it is positioned to cover the defect and the area immediately surrounding it. One of the surfaces of the mesh is in direct contact with the body wall while the other surface is facing the laparoscopic instruments and the inside of the body cavity. At this stage the mesh may become displaced and lose its orientation and spatial location as well as the possibility of being folded over on itself. The surgeon needs to make certain that the mesh is completely spread out and fully covers the target area with no extra folding on itself and with complete contact between the body tissue coverage and the target area. It is difficult for the laparoscopic instruments to grasp the mesh, since the mesh is smooth, delicate with thin texture and in which one of its surfaces is in contact with internal tissue. Also, the scope or the camera used to visualize the inside of the body cavity has limited visualization of the far distance as well as impaired spatial orientation of the surgical field. This makes it even harder to manipulate the distant end of the mesh and to ensure its complete contact with the tissue.

Finally the mesh is secured into its place using different techniques that in part may involve passing several suture threads through the mesh and securing it with surgical knots to the subcutaneous tissue of the body. This may be done in a manner that the threads are not actually part of the mesh, but are tied and attached to the mesh before its insertion into the cavity and are passed after that through an incision made by a small laparoscopic grasping instrument that controls from the outside of the body cavity to grasp these threads from the inside to be finally tied with thread to the subcutaneous body area.

In accordance with the present invention, the mesh is manufactured with integrated threads that can be used to hold the mesh and make it easier to move, unfold, spread, as well as fixate to the body tissue.

In present practice, the minimal invasive surgery utilizes small ports to insert the instruments that are manipulated from outside of the body under the visualization of a scope "camera." These instruments with different tip types are designed to grasp, to cut or to dissect the tissue in order to conduct such interventions. The surgical mesh is inserted through the same ports and manipulated inside the body using different grabbers that are manipulated from outside the body. This step involves a lot of fine movements with the main objective that is to open and spread the mesh with a series of pushing and pulling over the target area. The mesh then is held using the laparoscopic instruments over the area of defect. Finally, the delicate mesh is secured into a finalized position as with the use of different techniques that in part might involves the use of surgical sutures, needles and threads.

The mesh is unfolded from its insertion rolled shape and is spread and finally adjusted with a series of pulling and pushing from different sides to fit exactly over the area of defect. Until this step, the grasping process is feasible because the laparoscopic instruments are holding the mesh from its two surfaces with the aid of two jaws that act as forceps.

After the mesh is delivered over the area of defect, it is applied directly where it should cover the defect and the area around it. One of the surfaces of the mesh is in direct contact with the body wall while the other surface is facing the laparoscopic instrument and the inside of the body cavity. At this time, the mesh may become displaced and lose its orientation as well as becoming folded over onto itself so that a surgeon needs to make sure that the mesh is completely spread as well as fully covering the target area with no excessive covering or more folding on itself and complete contact between the body tissue and the mesh surface. At this time, it is even more difficult for the laparoscopic instruments to grasp the mesh since the mesh is smooth, delicate with a thin texture and in which one of its surfaces is in contact with the body tissue. Also, the scope of the camera used to visualize the inside of the body cavity has limited visualization from the far distant view as well as impaired spatial orientation of the surgical field. Thus, it makes it even more difficult to manipulate the distant end of the mesh and to ensure its complete contact with the tissue.

Finally, the mesh is secured into its place using techniques that may involve passing several suture threads through the mesh and secure it with surgical knots to the subcutaneous tissue of the body. This may be done so that these threads are not actually part of the mesh but are tied and attached to the mesh before its insertion through an incision made for laparoscopic grasping instruments.

In order to improve and facilitate surgical procedures, Applicants have developed a mesh which can be more easily manipulated during laparoscopic procedures as well as limiting the use of surgical suture needles with its attached thread. The idea is to manufacture a surgical mesh with integrated threads that can be used to hold mesh and make it in the form required. In the present invention, the mesh for different patients is produced in different sizes to fit over the abdominal wall defects. For example, one of the anatomical types of mesh is designed that is oblong or square in shape with one corner of it being eliminated and giving it a semicircular opening. The other borders are complete in the desired shape. The reason for this is to just cover the defect without any coverage of the parts of the defected area along this curved side. The purpose is to avoid a weak point where recurrence of the defect might ensue.

The aim of the surgical mesh used in hernia repair is to reinforce the abdominal wall without reducing the mobility by excessive scarring. Surgical meshes are manufactured using different methods like knitting, weaving and so on. Different classifications of meshes are available, in which it can be made from monofilaments of multifilament. Also the mesh can be classified according to density, in which it is classified into heavyweight (HW) for densities above 80 g/m$^2$ or lightweight (LW) for densities below 50 g/m$^2$. In addition, materials with a density between 50 and 80 g/m$^2$ are designated medium weight (MW).

Other classification depends on the spacing between the constituting filaments or what is called pore size. This classification involves either a totally macro-porous mesh having a pore size >75 microns, totally micro-porous meshes with pore size of <10 microns, and a combination of such. Also, it can be manufactured in single or multilayers. All these features: filament composition, mesh weaves and the spatial arrangement of the filaments, along with pore size will determine the mechanical anisotropic behavior of a surgical mesh.

A surgical mesh with a filament count between 100 to 500+/−10% denier will be of an acceptable measurement in which its thickness associated with its flexibility will be of crucial object keeping in mind that the thinner the mesh the more its flexibility but in the same time the harder it is to handle. Also, macro-porous mesh having a filament spacing of 1 of more mils will be of optimum function in which it will aid in reduction of the amount of foreign material persisting in the host. In the other side, utilizing the component of thread per inch would affect the overall orientation of the mesh and its final disposition as a macro- (large) or micro-porous (small) mesh together with its overall mesh size. The best description of such is macro-pores having a spacing between the overall threads or filaments constituting the mesh of more that 75-micron to 1 mills and the micro-pore having a spacing between the overall threads or filaments constituting the mesh of less than 10 microns.

The final product can have many options available to constitute and build a mesh, keeping in mind that the new trend is to have a macro-porous, lightweight, and with good tensile strength (theoretically maximum of 32 N/cm and can be reduced to 16 N/cm).

In the present design that is directed to the use of surgical mesh in the correction of inguinal hernias and after reviewing the anatomy of the area to form an appropriate patch. In the present design different surgical meshes may have an oval or semicircular area of a defect that is located in the junction area between ⅓ and ⅔ of the mesh in the side that is designed to be secured distally. This will give a mesh with a side that has a point of the mesh designated to be secured distally. This will give a mesh with a side that is having a point of mesh free area with two remaining limbs of the mesh on either side of the defect as shown in FIG. 1.

The reason for this is to provide an area that will surround the vital organs. Thus these vessels are surrounded by the mesh without inducing pressure and in the same time the area that was previously not covered by the mesh is now covered. The elongated limb of the mesh that is represented above will pad that area and as part of the malleable mesh it has the freedom of malleability and movement to surround these structures and support the area around it for peritoneal fixation and padding.

One way to fixate the mesh to the abdominal wall is by the use of suture threads that are attached and tied to the mesh before its insertion into the body cavity. Another limitation difficulty is the smoothness of the mesh that makes it more difficult to manipulate especially after it is being laid on the abdominal wall with no loose area that eventually impairs the overall function of the mesh.

Figure 2:
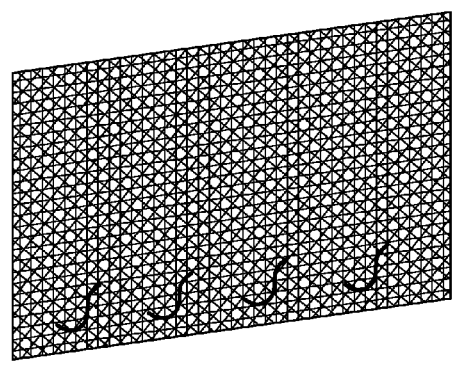
FIG. 2 is a schematic illustration of the surgical mesh with a plurality of fixation threads protruding from one side thereof.
Figure 3:
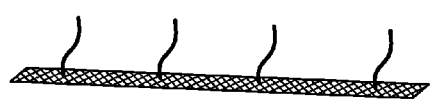
FIG. 3 is a schematic illustration of the protruding fixation threads and a plurality of grasping threads on the other side of the surgical mesh.
Figure 4:
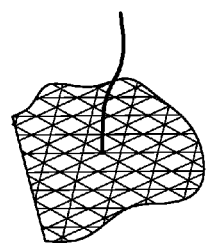
FIG. 4 is a schematic illustration showing the fixation threads on one side of the mesh.
Figure 5:
FIG. 5 is a schematic illustration of a mesh thread with an integral gripping thread extending outwardly without forming a gap in the mesh.
Figure 6:
FIG. 6 is a schematic illustration of a mesh thread with an integral grasping thread extending outwardly therefrom forming a gap in the mesh.
Figure 7:
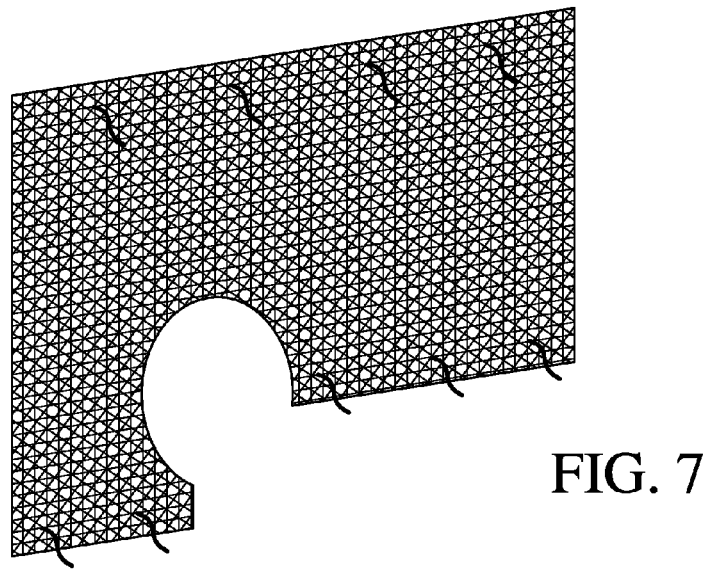
FIG. 7 is a schematic illustration of a mesh assembly to show a grasping threads extending outwardly from both sides of the mesh.
Figure 8:
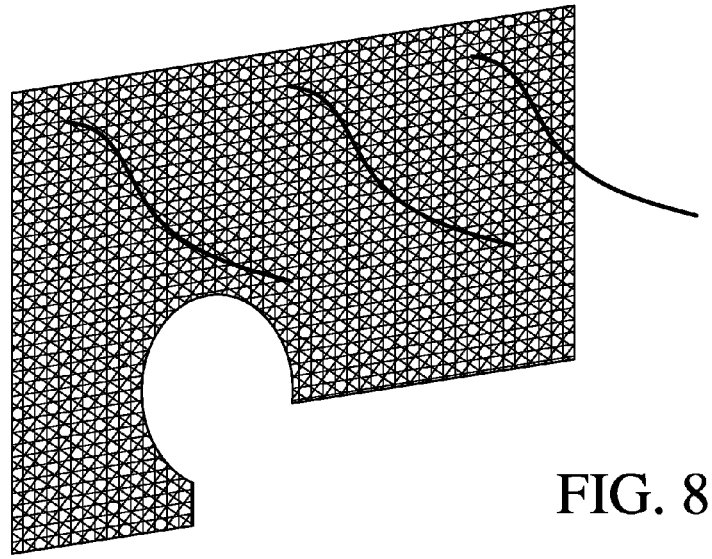
FIG. 8 is a schematic illustration of a surgical mesh with transfixing threads extending outwardly from one side thereof.

In any mesh system composed of several interlacing threads shape as well as orientation of the threads, a thread having its long length is an essential part of the mesh and is more stable with equal distribution of the tension. By the use of this intercalating threads, at the point where these threads are crossing each other (FIG. 4) it should give rise to a protruding thread that hangs freely on the surface of the mesh (FIGS. 2 and 3).

These grasping threads are manufactured in a length that varies from 0.5 cm to 1 cm. The reason for the presence of these short attached threads is to be used as graspers or as an area that will be used to hold while manipulating the mesh inside the body cavity. A surgical mesh is smooth and it is hard to be manipulated especially after its attachment to an abdominal wall. Another difficulty is that in a situation where the mesh folds over on itself, it becomes very difficult to manipulate and to unfold the mesh using laparoscopic instruments.

The grasping threads are designed to be held by the laparoscopic instrument. The orientation that each of these threads with their attachment being the intersection point of the original threads that makes the mesh lead to great mobility of the mesh as a whole. The disruption of these grasping threads varies depending on the shape of mesh. They are not to be strictly on one side of the mesh as in (FIGS. 2 and 3), but rather in different locations all around the surgical mesh that is to be decided upon manufacturing the mesh. Again keeping in mind that they are a continuation of the original threads not just a single attachment.

The use of the threads is to secure the mesh in place after the area of defect has been identified. The threads are tied to the mesh in different areas by the surgeon in preparing the mesh for insertion. The threads are hanging freely with varying lengths of 3 to 4 cm. A specialized laparoscopic instrument, having a small caliper with fine sharp tip and movable jaws is used. After that, the movable side jaw is opened. This jaw is closed to grasp a grasping thread. This is done several times in different locations so that more than one long thread is attached to the mesh inside the body cavity and one free end hanging freely in the outside surface to the skin. Later on these threads are tied in different ways to the subcutaneous tissue. The threads will function as transfixation threads and are a continuation of the threads that make the mesh. It is important to mention a color coding is implemented to differentiate the mesh material from the threads.

While the invention has been described in connection with its preferred embodiments it should be recognized that changes and modifications may be made therein without departing from the scope of the claims.

What is claimed is:

1. A surgical mesh of the type used in laparoscopic surgery, said surgical mesh comprising:
a compact roll of a planar overlay material of woven fibers and wherein said planar overlay material includes a plurality of outwardly extending integral grasping threads for grasping with a surgical instrument, and spreading over a tissue deficiency and further including a plurality of transfixing threads for transfixing said planar overlay material to surrounding tissue and in which said woven fibers are selected from the group consisting of nylon, polyester, and propylene fibers and mixtures thereof and in which said outwardly extending grasping threads for grasping have a length of between about ½ to 1 cm and the transfixing threads having a length of about 3 cm to 4 cm and in which said woven fibers are multifilaments and in which the multifilaments of the mesh are in the range of 100 to 500 +/−10% denier and in which the mesh is macro-porous having a pore size greater than 75 microns.

2. A surgical mesh of the type used in laparoscopic surgery according to claim 1, in which the plurality of outwardly extending integral threads for gripping extend outwardly from a single side of said planar overlay material and wherein said outwardly extending integral threads for transfixing said overlay material extend outwardly from an opposite side of said overlay material.

3. A surgical mesh of the type used in laparoscopic surgery according to claim 1, in which said outwardly extending integral threads for gripping extend outwardly from both sides of said planar overlay material.

* * * * *